United States Patent [19]

Ester, deceased et al.

[11] 3,960,672
[45] June 1, 1976

[54] CONTINUOUS DISTILLATION PROCESS FOR PURIFYING ALKANOLS

[75] Inventors: Wilhelm Ester, deceased, late of Herne; by Margarete Ester, nee Berkemann, heir, Herne; by Brigitte Lovis, nee Ester, heir, Munster; by Wolfgang Ester, heir, Herne; Wilhelm Heitmann, Herne, all of Germany

[73] Assignee: Veba-Chemie AG, Gelsenkirchen-Buer, Germany

[22] Filed: June 21, 1974

[21] Appl. No.: 481,943

Related U.S. Application Data

[63] Continuation of Ser. No. 223,345, Feb. 3, 1972, abandoned.

[30] Foreign Application Priority Data

Feb. 9, 1971 Germany............................ 2106073

[52] U.S. Cl.................................... 203/37; 203/18; 203/83; 203/85; 260/643 R
[51] Int. Cl.²........................................... B01D 3/34
[58] Field of Search.................... 260/643 R, 643 E; 203/18, 19, 37, 82–85

[56] References Cited
UNITED STATES PATENTS

| | | | |
|---|---|---|---|
| 2,454,734 | 11/1948 | Darlington et al..................... | 203/82 |
| 2,695,867 | 11/1954 | Chambers............................. | 203/18 |
| 3,014,971 | 12/1961 | Wilson.............................. | 260/643 E |
| 3,156,629 | 11/1964 | Ester.............................. | 260/643 E |
| 3,445,345 | 5/1969 | Katzen et al......................... | 203/85 |

*Primary Examiner*—Jack Sofer
*Assistant Examiner*—Frank Sever
*Attorney, Agent, or Firm*—Burgess, Dinklage & Sprung

[57] ABSTRACT

Pure $C_1$–$C_3$ alkanols are prepared from crude water containing alcohols in a continuous distillation process which includes an extractive distillation zone into which water and crude alcohols are introduced and from which is removed an impurities stream and a dilute aqueous alcohol stream; an alcohol concentration zone into which is introduced a dilute alcohol stream from the extractive distillation zone from which is withdrawn pure concentrated alcohols, a low boiling impurities stream and a high boiling impurities stream; and an impurities concentration zone into which is introduced the impurities stream from the extractive distillation zone and the high and low boiling impurities streams from the alcohol concentration zone from which is withdrawn high and low boiling impurities and an alcohol containing stream which is recycled to the extractive distillation zone with the crude alcohols. Aqueous alkali solution is injected into the alcohol concentration zone above the point at which the high boiling impurities stream is withdrawn and below the point from which pure concentrated alcohols are withdrawn. In addition, the sump product from the alcohol concentration zone is discarded or neutralized and recycled to the upper portion of the extractive distillation zone.

8 Claims, 1 Drawing Figure

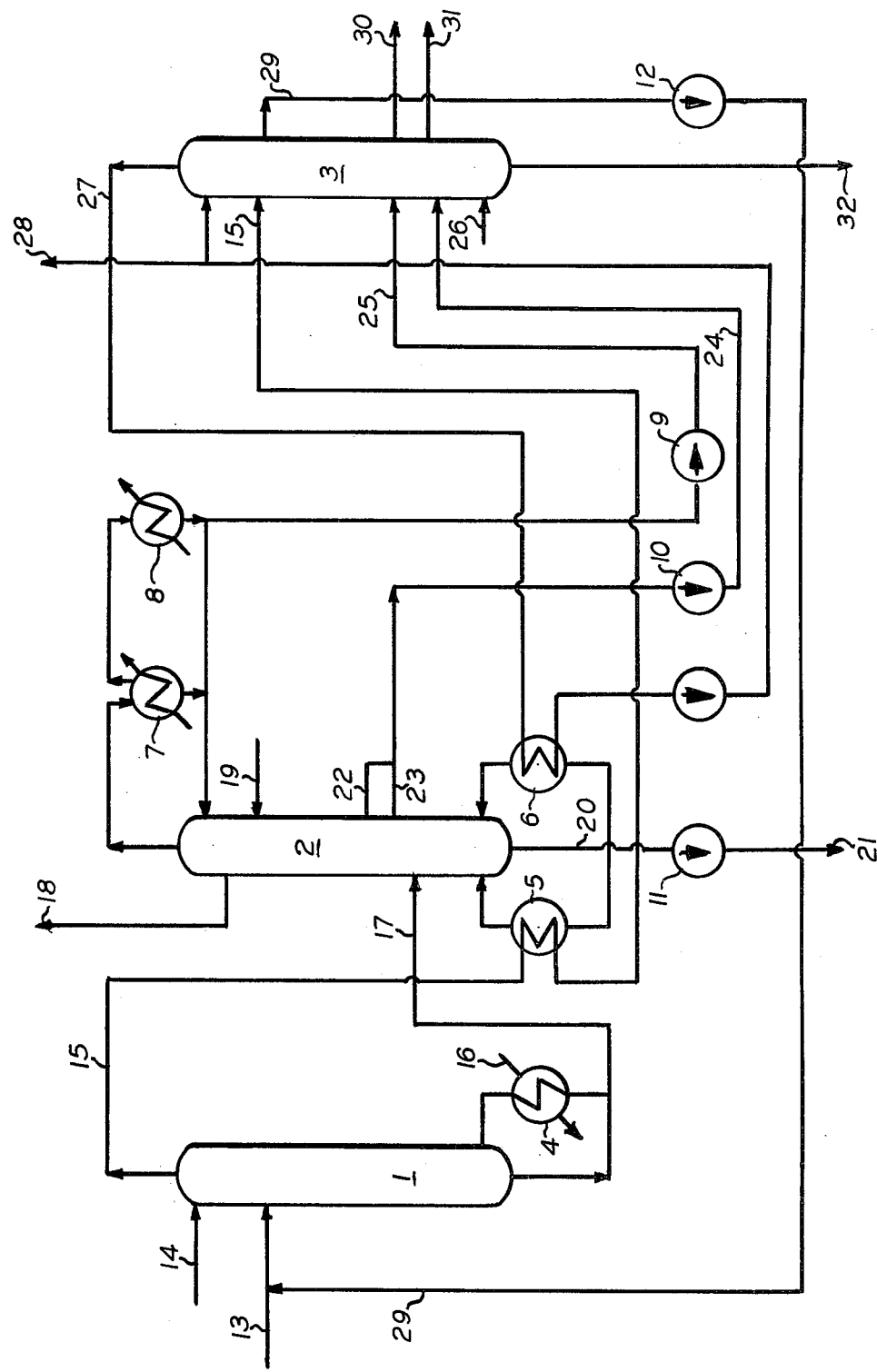

CONTINUOUS DISTILLATION PROCESS FOR PURIFYING ALKANOLS

This is a continuation of application Ser. No. 223,345, filed Feb. 3, 1972, now abandoned.

BACKGROUND

This invention relates to a distillation process for purifying crude $C_1$–$C_3$ alkanols. More particularly, this invention relates to an improved process for preparing pure $C_1$–$C_3$ alkanols using aqueous alkali at a certain stage of a three zone distillation operation.

Saturated $C_1$–$C_3$ crude alcohols obtained by various methods through dry distillation, fermentation or synthesis, are contaminated with substances such as ethers, acids, aldehydes, ketones and esters, the removal of which often entails considerable difficulty.

Conventional purification processes previously used were generally such that the alcohol-containing fluid to be purified was introduced into a distillation column into whose bottom end was fed the amount of steam required for the removal of the impurities. The impurities were then removed at the top of the zone, while the partially purified alcohol was drawn out at a lower level and subjected to further purification in a rectifying apparatus. The impurities fraction however still contain appreciable amounts of alcohol which is usually difficult to separate.

In the prufication of alcohol originating from the catalytic hydration of ethylene, it is also possible to proceed by first adjusting the pH value of the reaction product to between 6 and 9 by the addition of alkaline substances, then performing a fractional distillation, hydrogenating the ethanol solution thus obtained in the presence of a nickel catalyst, and then again distilling it fractionally. While this process is complicated and expensive, the first process mentioned has the main disadvantage that considerable amounts of low-grade alcohols are produced. It has therefore been suggested that the purification be performed in the following manner.

The crude alcohol is fed into the middle of a zone, the amount of steam required for the extraction of the impurities is injected into the lower part, and pure water or water containing a small amount of alcohol is sprinkled in the upper part of the zone, in such a manner that the alcohol concentration in the upper part of the zone does not exceed 20% by volume. Then the impurities are drawn off at the top of the zone in concentrated form and returned to the top tray of the zone, although a portion of the condensate is drawn off in such a manner that the amount removed corresponds to the amount of impurities contained in the starting liquid. At the upper part of the zone, then, a zone of highly concentrated impurities forms.

This process can be improved by providing a decanting tray at the top of the column in order to achieve a separation of the liquid that gathers there into an upper layer rich in impurities, which is drawn off, and a lower layer having a lower content of impurities. In this manner it is said to be possible to achieve yields of more than 99.5% of pure alcohol.

Actually, however, it has been found that the process is not suitable for the purification of highly contaminated synthesis alcohols containing particularly great amounts of ether and aldehydes, because separation of the liquids by decantation is not possible since they do not separate sufficiently by gravity.

For the prevention of corrosion phenomena, and to improve the purifying action, it is furthermore desirable to add alkali to the sprinkling water which comes from the bottom part of a second zone and is recirculated to the head of the first zone.

In this case, however, resin-like products are formed due to the aldehyde content of the crude alcohol, some of them being deposited in the form of incrustations on the trays of the zone and resulting in an impairment of the action of the zone.

These phenomena are particularly pronounced when the starting ethylene has not been subjected to any separate hydrogenation prior to the synthesis, because the acetylene contained in the ethylene is largely transformed to acetaldehyde, and then the above-described severe incrustation and resinification develops, which furthermore renders safe and reliable operation impossible. It is therefore necessary to shut down the plant from time to time and perform a difficult and expensive cleaning operation.

A process is also known for obtaining alcohol from mixtures containing crude alcohol, which is characterized by the fact that into the middle section of a first distillation tower, which forms a zone for extraction distillation, there is introduced an input current containing a saturated, aliphatic alcohol of no more than three carbon atoms containing lower and higher boiling impurities as accompanying substances, water is introduced into the upper section of the first distillation tower, a current containing virtually all the impurities is drawn from the head of the first distillation tower, a dilute aqueous current containing the alcohol in concentrations of about 5 weight percent to about 10 weight percent plus smaller amounts of the lower and higher boiling accompanying substances is taken from the bottom of the first distillation tower, the dilute, aqueous current taken from the bottom of the first distillation tower is delivered to a second distillation tower forming a rectification or alcohol concentration zone, an alcohol product current containing the alcohol in high concentration and in purified form is taken from the upper section of the second distillation tower, a purification current containing the lower boiling impurities is taken from the head of the second distillation tower, at least one purification current containing the higher boiling impurities is taken from the middle section of the second distillation tower, the purification currents from the second distillation tower and the current taken from the head of the first distillation tower are transferred to a third distillation tower forming a zone for the concentration of the impurities, the lower and higher boiling impurities are taken from the third distillation tower, and by the fact that a current containing alcohol is taken from the third distillation tower and recycled together with the input current to the first distillation tower. The products of this process, however, fail to meet the purity requirements of a number of applications. Such requirements can, however, be met by proceeding in accordance with the present invention.

SUMMARY

The present invention provides an improved continuous distillation process for preparing pure $C_1$–$C_3$ alkanols from crude water containing alkanols wherein a. crude alkanols and water are introduced into an extractive distillation zone and an impurities stream and a dilute aqueous alkanol stream is withdrawn from said extractive distillation zone;
b. the dilute alkanol stream from said extractive distillation zone is introduced into an alkanol concentration zone from which is withdrawn pure concentrated alkanols, a low boiling impurities stream and a high boiling impurities stream; and
c. the impurities stream from the said extractive distillation zone and said high and low boiling impurities streams from said alcohol concentration zone are introduced into an impurities concentration zone from which is withdrawn high and low boiling impurities and a stream containing alkanols which is recycled to said extractive distillation zone with said crude alkanols.

The improvement comprises introducing aqueous alkali solution into said alcohol concentration zone at a point above the point from which said high boiling impurities stream is withdrawn and below the point from which pure concentrated alkanols are withdrawn.

DESCRIPTION OF THE DRAWING

The accompanying drawing is a diagrammatic flow sheet of a preferred embodiment of the process of the invention.

DESCRIPTION

In a preferred embodiment, especially pure $C_1$–$C_3$ alcohols can be prepared from water-containing crude alkanols by continuous distillation in three distillation zones or columns which comprises a. feeding to the middle section of the first zone a mixture of a $C_1$–$C_3$ alkanol, water and lower and higher boiling impurities,
b. introducing water into the upper section of the first zone,
c. removing a current containing most of the impurities from the head of the first zone,
d. withdrawing a dilute, aqueous current containing the alcohol in concentrations of about 5 weight percent to about 10 weight percent plus lesser amounts of higher and lower boiling accompanying substances from the bottom of the first zone,
e. feeding the dilute, aqueous current withdrawn from the bottom of the first zone in step d to the second zone,
f. withdrawing the finished product from the upper section of the second zone,
g. removing a purification current containing the low boiling impurities from the head of the second zone,
h. withdrawing at least one purification current containing the higher boiling impurities from the middle section of the second zone,
i. feeding the purification currents from the second zone (steps g and h) and the current taken from the head of the first zone (step e) to a third zone,
j. removing the lower boiling and the higher boiling impurities from the third zone, and
k. removing from the third zone a current containing an alcohol and recycling same together with the input current to the first zone (step a).

Aqueous alkali solution is injected above the point of removal of the higer boiling impurities (step h) and the sump product from the second zone is discarded or, after neutralization if desired, is fed to the upper section of the first zone.

The process of the present invention can be performed for the purification both of methanol (dry distillation and synthesis product) and ethanol (of synthetic origin or fermentation alcohol) and of n-propanol and isopropanol.

For the refinement of the partially purified $C_1$–$C_3$ alkanols, aqueous solutions of alkali hydroxides are used. For economic reasons, however, sodium hydroxide and/or potassium hydroxide are preferred. An approximately 20 weight percent aqueous NaOH is especially preferred, since it has a melting point of −25°C. The aqueous alkali solution is best used in such an amount that 0.01 to 10.0, preferably 0.1 to 1.0, kilograms of alkali hydroxide are used per ton of crude alcohol. It is preferable to use as the aqueous alkali solution one which has the lowest or nearly the lowest melting point for the alkali hydroxide/water system. By nearly the lowest melting point is meant a melting point that differs from the lowest by only 10 percent.

It is desirable to introduce the aqueous alkali solution at a point that is sufficiently below the point of removal of the finished product to prevent mixing with the finished product.

The system of apparatus required for the performance of the process of the invention is shown in the appended flow diagram which is described in detail in Control 1 and Example 1.

The three zones are operated in such a manner that an extraction distillation is performed in the first. The second zone serves for rectification and alcohol concentration and the third for concentration of the impurities.

The special advantages of the process of the invention lie in an appreciable improvement of the odor rating of the alcohols and in the removal of unidentified impurities, which results in an increase in the permanganate number which serves as a special criterion for judging the purity of alcohols.

The technical advance achieved by the process of the invention is shown by the following examples.

CONTROL 1 (for purposes of comparison)

A crude alcohol obtained by direct catalytic hydration of ethylene in the gaseous phase and having an ethanol content of 13.5 weight percent was fed at a rate of 33.0 tons per hour through line 13 to a point slightly above the center of the zone 1. The zone was operated at a pressure of 5 atmospheres gauge. The steam requirement was 12.0 tons per hour. From the head of the zone the vapors were fed through line 15 to the condenser 5 and from there, after condensation, they passed on to zone 3. 35 cubic meters per hour of extraction water were delivered through line 14 to the head of zone 1. The alcohol thus purified and gathering in the sump of zone 1 was delivered through line 17 to the rectifying zone at approximately the 16th tray, where it was strengthened and it was removed about 6 trays below the head 18 as a 94.6 weight percent alcohol. The vapors at the head of zone 2 were partially condensed in condenser 7 and the remainder was fully condensed in condenser 8. Nearly all of the condensate was recycled to the zone. At the 3rd and 5th tray above the inlet, 500 l/h was drawn off through each of lines 22 and 23 and driven by the pump 10 through line 24 into zone 3. All of the water that had been freed of the alcohol and gathered in the sump of zone 2 was purged off.

The following was fed into zone 3:
500 l/h to the 14th tray via line 24
7000 l/h to the 16th tray via line 25
200 l/h to the 40th tray via line 15
6500 kg of steam directly into the sump of the zone. The zone was operated at a pressure of 7 atmospheres gauge. The vapors were carried from the head of the zone through line 27 to condenser 6, and the condensate was recycled to the head of the zone. A partial stream 28 was purged out. Just above the center of the zone an alcohol-rich product was recycled through line 29 back to zone 1. Butanols and other higher boiling products were purged at a lower level through line 30 and/or 31 and delivered to a separate process. The distillation yield amounted to 96.4%.

The finished product, which was drawn off through 18, had the following properties (determined according to the analysis methods of the Federal Brandy Monopoly).

| | |
|---|---|
| Concentration: | 94.6 weight percent |
| Acetaldehyde: | 4.7 mg/l |
| Fusel Oils: | 5 mg/l |
| Acid (as acetic acid): | 2 mg/l |
| Ester (as acetic ester): | 31 mg/l |
| Evaporation residue: | 4 mg/l |
| Permanganate number (The method is described in Analytical Chemistry, 24 (1952), 1658–60.) | 6 minutes |

As another criterion of purity, the light absorption in the ultraviolet range was determined. For a depth of 4 cm, measured against distilled water, it was as follows:

| Wavelength (millimicrons) | Extinction |
|---|---|
| 250 | 0.55 |
| 230 | 1.5 |
| 220 | >2.0 |
| 210 | >2.0 |

The product had a slightly acrid odor.

EXAMPLE 1 (process of the invention)

The distillation was conducted as described in Control 1. In addition, 10 liters per hour of a 20 weight percent caustic soda solution was continuously injected through line 19, four trays below the point of removal of the finished product.

The distillation yield amounted to 96.5%.

The finished product had the following characteristics:

| | |
|---|---|
| Concentration: | 94.5 weight percent |
| Acetaldehyde: | 0.8 mg/l |
| Fusel Oils: | 5 mg/l |
| Acid (as acetic acid): | 0 mg/l |
| Ester (as acetic ester): | 10 mg/l |
| Evaporation residue: | 4 mg/l |
| Permanganate test: (The method is described in Analytical Chemistry, 24 (1952), 1658–60.) | 62 minutes |

In addition, the ultraviolet light absorption was determined. It amounted to the following (same conditions as Control 1):

| Wavelength (millimicrons) | Extinction |
|---|---|
| 250 | 0.03 |
| 230 | 0.12 |
| 220 | 0.23 |
| 210 | 0.39 |

The mixture was clearly better. The odor can be described as neutral.

The distillation yield can be further improved by subjecting the partial stream containing impurities, which is the condensate of the vapors of the third zone, to a repeated extraction distillation with water in zone 4, which is connected to line 28. The resultant water containing alcohol can be recycled through line 13.

EXAMPLE 2 (process of the invention)

The distillation of the crude alcohol was performed as in Control 1. At the tenth tray down from the head of the zone, through line 19, 10 liters per hour of a 20 weight percent caustic soda solution were continuously fed into zone 2. 450 kg/h of the condensate of the vapors of zone 3 were fed through line 28 into the central part of an extraction zone. 3000 kg per hour of water was pumped to the head of the zone. 150 kg/h of steam was fed directly into the sump of the zone. The zone was operated at a pressure of 1 atmosphere gauge pressure. The condensate produced was completely condensed and the condensate was separated in a settling tank into two layers. The upper layer contained mainly ether. It was drawn off and can be used, if desired, as a raw material for the recovery of ether. The bottom layer — mostly water — returns to the center part of the zone. The ethanol-containing water is pumped from the sump of the zone back into line 13.

The distillation yield amounted to 99.7%. The quality of the alcohol produced was the same as that of Example 1.

What is claimed is:

1. In a continuous distillation process for preparing pure $C_1$–$C_3$ alkanols from crude water-containing alkanols wherein:
    a. crude alkanols containing water and impurities which are lower and higher boiling relative to said alkanols, are introduced to the middle section of an extractive distillation zone and a stream containing said impurities is withdrawn overhead and a dilute aqueous alkanol stream is withdrawn from the bottom of said extractive distillation zone;
    b. the dilute alkanol stream from the bottom of said extractive distillation zone is introduced to the lower section of an alkanol distillation zone from which are withdrawn a pure concentrated alkanol stream from an upper section, a stream containing low boiling impurities from a middle section and a stream containing high boiling impurities overhead;
    c. the overhead stream from said extractive distillation zone and said streams containing high and low boiling impurities from said alkanol distillation zone are introduced into a zone for distilling said impurities from which are withdrawn a stream containing high boiling impurities from a lower section, a stream containing low boiling impurities overhead and a stream containing alkanols from a middle section, the latter being recycled to said extractive distillation zone with said crude alkanols, the improvement which consists of introducing aqueous alkali hydroxide solution into said alkanol distillation zone at a single point which is above the point from which the stream containing high boiling impurities is withdrawn and below the point from which pure concentrated alkanols are withdrawn.

2. Process of claim 1 wherein the sump product from said alkanol distillation zone is discarded.

3. Process of claim 1 wherein the sump product from said alkanol distillation zone is neutralized and recycled to said extractive distillation zone.

4. In a continuous distillation process for preparing pure $C_1$–$C_3$ alkanols from crude water-containing alkanols in three distillation zones which comprises:
   a. feeding to the middle section of the first distillation zone a mixture of a $C_1$ to $C_3$ alkanol, water and impurities which are lower and higher boiling relative to said alkanol;
   b. introducing water into the upper section of the first zone;
   c. removing from the head of the first zone a stream containing most of said impurities;
   d. withdrawing from the bottom of the first zone a dilute aqueous stream which contains the alcohol in concentrations of about 5 to about 10 percent by weight and smaller amounts of said impurities relative to the amount of impurities in the stream removed in step (c);
   e. delivering the dilute aqueous stream taken from the bottom of the first zone to the lower section of the second distillation zone;
   f. withdrawing pure alkanols from the upper section of the second zone;
   g. removing at the head of the second zone a stream containing the low-boiling impurities;
   h. removing from the middle section of the second zone a stream containing the higher boiling impurities;
   i. transferring streams (g) and (h) from the second zone and the stream (c) from the head of the first zone to the third distillation zone;
   j. removing the lower and the higher boiling impurities from the third zone; and
   k. removing a stream containing alkanols from the third zone and recycling same to the first zone, the improvement which consists of introducing aqueous alkali hydroxide solution into the second zone at a single point which is beneath the point of removal of pure alkanols and above the point of removal of higher-boiling impurities and withdrawing a water-containing sump product from the second zone.

5. Process of claim 4 wherein the water-containing sump product from the second zone is neutralized and recycled to the upper section of the first distillation zone.

6. Process of claim 4 wherein aqueous alkali hydroxide solution is used in an amount of 0.01 to 10.0 kg of alkali hydroxide per ton of pure alkanol recovered.

7. Process of claim 4 wherein the aqueous alkali hydroxide solution is one which has the lowest or nearly the lowest melting point for the alkali hydroxide/water system.

8. Process of claim 4 wherein the stream (g) from the third zone which contains the low boiling impurities is subjected to an extractive distillation with water in a fourth distillation zone in the series.

* * * * *